United States Patent [19]

Owens et al.

[11] Patent Number: 5,618,997

[45] Date of Patent: Apr. 8, 1997

[54] SAMPLING APPARATUS FOR A SOLIDIFIED BODY

[75] Inventors: Ivan F. Owens, Egremont; Dugald R. Sperry-Lamb, Haverigg, both of England

[73] Assignee: British Nuclear Fuels plc, Warrington, United Kingdom

[21] Appl. No.: 6,847

[22] Filed: Jan. 21, 1993

[30] Foreign Application Priority Data

Jan. 22, 1992 [GB] United Kingdom .................. 9201302

[51] Int. Cl.$^6$ ............................................ G01N 1/12
[52] U.S. Cl. ............................ 73/864.55; 73/864.56; 73/864.59; 73/DIG. 9
[58] Field of Search ........................ 73/864.51, 864.52, 73/864.53, 864.55, 864.56, 864.57, 864.59, DIG. 9, 863.41, 863.42, 863.43, 863.51, 863.52

[56] References Cited

U.S. PATENT DOCUMENTS

| | | | |
|---|---|---|---|
| 3,798,974 | 3/1974 | Boron | 73/864.59 |
| 3,915,002 | 10/1975 | Hance et al. | 73/864.55 |
| 3,950,992 | 4/1976 | Hance | 73/864.55 |
| 4,010,649 | 3/1977 | Falk | 73/864.55 |
| 4,060,000 | 11/1977 | Baker et al. | |
| 4,481,833 | 11/1984 | Bajek | 73/863.41 |
| 5,033,320 | 7/1991 | Baerts | 73/864.59 |

FOREIGN PATENT DOCUMENTS

| | | | |
|---|---|---|---|
| 1239547 | 7/1971 | United Kingdom . | |
| 1274618 | 5/1972 | United Kingdom | 73/864.55 |
| 2205399 | 12/1988 | United Kingdom . | |

*Primary Examiner*—Hezron E. Williams
*Assistant Examiner*—Nashmiya Ashraf
*Attorney, Agent, or Firm*—Nixon & Vanderhye P.C.

[57] ABSTRACT

An apparatus for sampling a solidified body in a vessel. The apparatus includes a tubular outer member and a tubular inner member slidable one within the other in close telescopic relationship. A datum location is provided for locating the inner member in an axial and radial datum location in the outer member. In the datum location the outer and inner members define a plurality of longitudinally displaced transverse holes therethrough to permit flow of the body whilst in a fluid state from the outside of the outer member to the inside of the inner member. A sample of the body is provided in the inner member. The solidified body may comprise vitrified highly radioactive waste or intermediate level radioactive waste incorporated in a setting material such as cementitious grout.

9 Claims, 1 Drawing Sheet

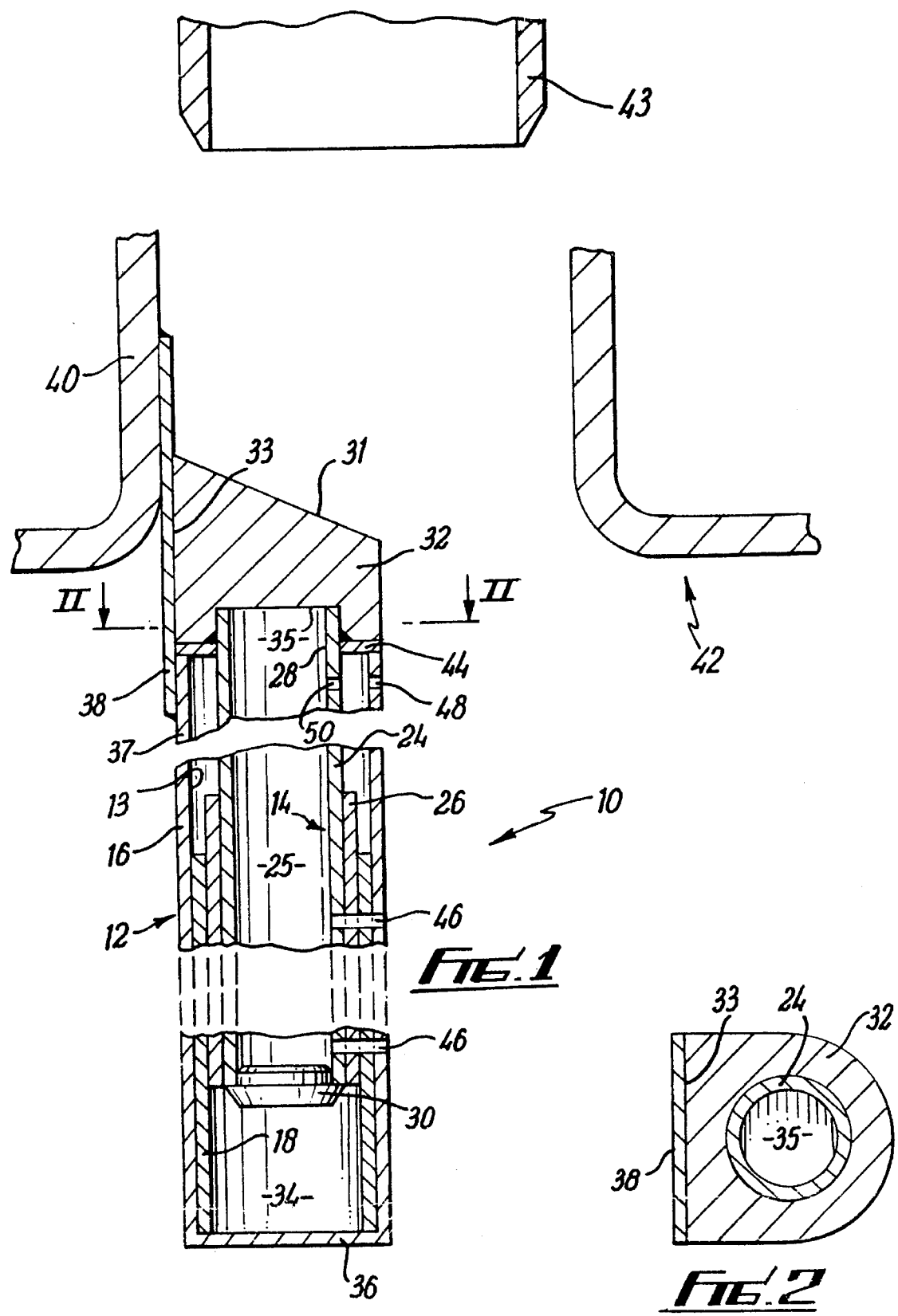

SAMPLING APPARATUS FOR A SOLIDIFIED BODY

BACKGROUND OF THE INVENTION

1. Field of the Invention

This invention relates to a sampling apparatus and more particularly to an apparatus for providing a sample of a solidified body containing radioactive waste from a nuclear reprocessing plant.

2. Discussion of Prior Art

It is the practice in the nuclear reprocessing industry to contain radioactive waste in a solidified body for subsequent long term storage. It may be necessary at some time or other for a sample of the body to be produced for analysis.

There are a large number of known devices for sampling bulk media. For example, GB 1239547 describes a device for sampling a molten metal from a furnace, whilst GB 2205399 discloses an apparatus for taking samples from a bulk granular material. Both of these aforementioned samplers are designed for operation on fluid bulks and are immediately withdrawn after collection of the sample.

SUMMARY OF THE INVENTION

According to the present invention there is provided an apparatus for sampling a solidified body in a vessel, the apparatus comprising a tubular outer member and a tubular inner member slidable one within the other in close telescopic relationship, means for locating the inner member in an axial and radial datum location in the outer member, and the outer member and the inner member in the datum location defining a plurality of longitudinally displaced transverse holes therethrough to permit flow of the body whilst in a fluid state from the outside of the outer member to the inside of the inner member, thereby to provide a sample of the body in the inner member.

Although the sampler of the present invention is, like the prior art samplers described above, designed to sample a fluid bulk, the sample is withdrawn at a later time when the bulk medium has solidified. A sample taken by the apparatus of the present invention will therefore have the same thermal history as that of the bulk medium which is not the case with the metal sampler disclosed in GB 1239547. The sampler of the present invention is a passive device which, once located in place, offers the option of being withdrawn or left in situ for an indefinite period of time.

The sampler according to the present invention beneficially is suited to remote operation which is desirable to avoid human contact with hazardous environments.

The body sampled by the apparatus according to the present invention may comprise vitrified highly radioactive waste. Alternatively, the body may comprise intermediate level radioactive waste incorporated in a setting material such as a solidified cementitious grout.

Preferably, the outer member is disposed substantially upright and secured to an inlet to the vessel.

Desirably, the outer member comprises a round metal outer element and a round graphite inner element, and the inner member comprises a round metal inner element and a round graphite outer element.

In use of the apparatus of the invention once the vessel has been filled with the fluid body and after solidification thereof, the inner member may be withdrawn from the outer member to allow the sample therein to be examined.

BRIEF DESCRIPTION OF PREFERRED EMBODIMENT

The invention will now be further described by way of example only with reference to the accompanying drawing in which:

FIG. 1 shows a side medial sectional view of a glass sampling apparatus, and FIG. 2 shows a view on the line II—II of FIG. 1.

DETAILED DESCRIPTION OF PREFERRED EMBODIMENT

Referring now to FIGS. 1 and 2, a sampling apparatus 10 is shown and comprises a tubular outer member 12 of circular cross-section and a tubular inner member 14 of circular cross-section located in close telescopic sliding relationship in the outer member 12 and defining an annular space 13 therebetween. The outer member 12 comprises a steel outer element 16 in which a shorter graphite inner element 18 locates as an interference fit. The inner member 14 comprises a steel inner element 24 having a bore 25 and a shorter graphite outer element 26 as an interference fit about the steel inner element 24. A steel frusto-conical plug 30 closes the lower end of the steel inner element 24, and a space 34 is defined between the plug 30 and a closed end 36 of the steel outer element 16. The steel outer element 16 is welded at its upper end 37 to a steel support member 38 which is itself welded to an inlet 40 of a steel vessel 42 for the incorporation of radioactive waste in a solidified body. The body in a fluid state is fed into the vessel 42 from a dispenser 43. The steel inner element 24 at its upper end 28 is welded to a steel cap 32 which has a flat side 33 adjacent to the support member 38, a sloping upper surface 31 and a central circular recess 35 in which the steel inner element 24 locates. The cap 32 rests on a graphite washer 44 supported by the upper end 37 of the outer steel element 16 to establish a datum location of the inner member 14. In this datum location, a number (eg, nine) of longitudinally displaced transverse holes 46 extend through the outer member 12 and the inner member 14 below the upper ends of the graphite inner element 18 and the graphite outer element 26 to allow flow therethrough from the outside of the outer member 12 to the bore 25 of the steel inner element 24. A vent hole 48 from the annular space 13 extends through the upper end 37 of the steel outer element 16, and a vent hole 50 between the bore 25 and the annular space 13 extends through the upper end 28 of the steel inner element 24.

In operation for the vitrification of highly active radioactive waste and with the inner member 14 in the datum location, fluid molten glass is poured from the dispenser 43 through the inlet 40 into the vessel 42 and retains sufficient mobility to successively overflow through the holes 46 into the bore 25 so that a molten glass sample builds up in the bore 25. After solidification of the glass in the vessel 42, the cap 32 is grasped by a clamp (not shown) and the cap 32 with the inner member 14 is extracted from the outer member 12, solidified glass in the holes 46 being sheared as the inner member 14 is withdrawn from the outer member 12. The glass sample is, therefore, retained in the bore 25 from which it can be subsequently recovered, for example by mechanical or chemical means, by remelting, or by dissolution of the glass sample.

The inner member 14 after withdrawal may be sectioned into a number of longitudinal portions to assist in recovering portions of the glass sample.

The holes 46 should not be so large that the molten glass forms glass bars which require considerable force to shear them. For molten glass, holes 46 of about 2 to 3 mm diameter should be satisfactory. To assist extraction of the inner member 14, a sharp downward blow may be applied to the cap 32 to compress the graphite washer 44 and shear the glass bars in the holes 46.

To assist extraction of the inner member 14, the collar 32 may be shaped to fit an extractor device (not shown), for example by defining a screw threaded spigot to fit a corresponding portion of an extractor.

When intermediate level radioactive waste is to be incorporated in a setting material such as a solidified cementitious grout, the grout before setting and in a fluid state is poured from the dispenser 43 into the vessel 42 where solidification of the grout takes place. A sample of the solidified grout may be extracted in the inner member 14 in a similar manner to that described in relation to the vitrification of highly active waste.

We claim:

1. An apparatus for sampling a fluid material which subsequently solidifies into a solidified body in a vessel, the apparatus comprising:

a tubular outer member and a tubular inner member slidable one within the other along a longitudinal axis extending through the members in close telescopic relationship, means for locating the inner member in an axial and radial datum location in the outer member, and the outer member and the inner member in the datum location including a plurality of holes displaced along said longitudinal axis, each hole extending transversely through said outer and inner members for permitting flow of the body whilst in a fluid state from the outside of the outer member to the inside of the inner member, thereby to provide a solidified sample of the body in the inner member which is removed from the vessel at a time after the body has solidified.

2. Apparatus as claimed in claim 1, wherein the outer member comprises a round metal outer element and a round graphite inner element, and the inner member comprises a round metal inner element and a round graphite outer element.

3. Apparatus as claimed in claim 2, wherein the outer member is disposed substantially parallel to the longitudinal axis.

4. Apparatus as claimed in claim 2, and comprising also a frusto-conical plug which closes a base end of the inner member.

5. Apparatus as claimed in claim 1, and wherein the locating means comprises a cap secured to the inner member and supported by the outer member, and a graphite annular element interposable between the cap and the outer member.

6. Apparatus as claimed in claim 5, wherein the outer member is secured to a support member adjacent to an inlet to the vessel.

7. Apparatus as claimed in claim 6, wherein the locating means includes the support member defining a datum surface, and the cap defining a complementary datum surface arrange to be adjacent to the support member datum surface, the support and the cap providing means to locate the outer and inner members respectively so as to define said longitudinally displaced transverse holes.

8. Method of using an apparatus as claimed in claim 1 for sampling a solidified body comprising one of vitrified highly radioactive waste and intermediate level radioactive waste incorporated in a setting material, said method comprising the steps of:

locating said apparatus at least partially within said fluid material;

permitting said fluid material to flow through said longitudinally displaced holes at least partially filling said tubular inner member;

permitting said fluid material at least partially filling said inner member to solidify providing said solidified sample; and moving said inner member relative to said outer member and withdrawing said solidified sample in said inner member.

9. The method as claimed in claim 8, wherein the setting material comprises a cementitious grout.

* * * * *